(12) United States Patent
Koerperick et al.

(10) Patent No.: US 9,146,189 B2
(45) Date of Patent: Sep. 29, 2015

(54) OPTICAL CELL WITH DISPOSABLE FLUID CARTRIDGE

(71) Applicant: ASL Analytical, Inc., Coralville, IA (US)

(72) Inventors: Edwin John Koerperick, North Liberty, IA (US); Jonathon Todd Olesberg, Iowa City, IA (US); Christine Esther Evans, North Liberty, IA (US); Mark Allen Arnold, Iowa City, IA (US); Gregory Allan Brower, Coralville, IA (US)

(73) Assignee: ASL Analytical, Inc., Coralville, IA (US)

( * ) Notice: Subject to any disclaimer, the term of this patent is extended or adjusted under 35 U.S.C. 154(b) by 0 days.

(21) Appl. No.: 14/631,914

(22) Filed: Feb. 26, 2015

(65) Prior Publication Data
US 2015/0247791 A1    Sep. 3, 2015

Related U.S. Application Data

(60) Provisional application No. 61/953,374, filed on Mar. 14, 2014, provisional application No. 61/946,170, filed on Feb. 28, 2014.

(51) Int. Cl.
| | |
|---|---|
| *G01J 5/02* | (2006.01) |
| *G01N 21/03* | (2006.01) |
| *G01N 21/359* | (2014.01) |
| *G01N 21/05* | (2006.01) |
| *A61M 1/36* | (2006.01) |
| *G01N 15/14* | (2006.01) |

(52) U.S. Cl.
CPC ............ *G01N 21/03* (2013.01); *G01N 21/0332* (2013.01); *G01N 21/359* (2013.01); *A61M 1/3693* (2013.01); *A61M 1/3696* (2014.02); *G01N 15/1404* (2013.01); *G01N 21/05* (2013.01); *G01N 2021/0321* (2013.01); *G01N 2021/0364* (2013.01); *G01N 2201/02* (2013.01); *G01N 2201/061* (2013.01)

(58) Field of Classification Search
CPC .......... G01N 2021/0364; G01N 21/05; G01N 15/1404; A61M 1/3693; A61M 1/3696
See application file for complete search history.

(56) References Cited

U.S. PATENT DOCUMENTS

| | | | |
|---|---|---|---|
| 5,184,192 A * | 2/1993 | Gilby et al. | 356/246 |
| 6,069,694 A | 5/2000 | VonBargen | |
| 6,542,231 B1 | 4/2003 | Garrett | |
| 7,369,226 B1 * | 5/2008 | Hewitt | 356/244 |
| 7,460,232 B2 | 12/2008 | Buijs et al. | |

(Continued)

FOREIGN PATENT DOCUMENTS

WO    2013072672 A2    5/2013

*Primary Examiner* — Christine Sung

(57) ABSTRACT

An optical apparatus with a single-use, disposable fluid flow cartridge and cell and associated optical interface is employed in determining characteristics of a fluid and/or suspended materials or cells contained therein which are introduced into the apparatus. The optical interface communicates electromagnetic radiation from an optical instrument through the fluid within the cell and to an appropriate sensor within the optical instrument. The interaction of the electromagnetic radiation with the fluid is measured by the signal generated by the sensor. Fluid present within the cell may be static or flowing, allowing both discrete sample measurements and monitoring of continuous processes.

34 Claims, 11 Drawing Sheets

(56) References Cited

U.S. PATENT DOCUMENTS

| | | |
|---|---|---|
| 7,961,310 B1 * | 6/2011 | Milosevic .................... 356/246 |
| 8,649,005 B2 | 2/2014 | Tormod |
| 8,760,658 B2 | 6/2014 | Hanlon et al. |
| 8,797,528 B2 | 8/2014 | Hanlon et al. |
| 2005/0117152 A1 * | 6/2005 | Barnikol et al. .............. 356/364 |
| 2012/0119101 A1 | 5/2012 | Wynn |
| 2012/0127456 A1 | 5/2012 | Frojdh et al. |

\* cited by examiner

OPTICAL CELL WITH DISPOSABLE FLUID CARTRIDGE

CROSS-REFERENCE TO RELATED APPLICATIONS

This application claims the benefit of U.S. provisional patent application No. 61/953,374, filed Mar. 14, 2014, for "Optical Flow Cell with Disposable Fluid Flow Cartridge," and U.S. provisional patent application No. 61/946,170, filed Feb. 28, 2014, for "Near Infrared Monitoring and Control." Such applications are incorporated herein by reference in their entirety.

STATEMENT REGARDING FEDERALLY SPONSORED RESEARCH OR DEVELOPMENT

This invention was made with government support under grant nos. 912828 and 1058434 awarded by the National Science Foundation. The government has certain rights in this invention.

BACKGROUND

The present invention relates to a single-use, disposable optical cell and cartridge with associated optical interface for use in conjunction with an optical instrument for analysis of fluid samples and the materials therein.

Measurement of characteristics of fluids by optical means is well-known in the art. The ability to characterize a fluid non-destructively is useful in many industrial and laboratory applications such as bioprocessing, chemical processing, food and beverage manufacturing, petroleum processing, and pharmaceutical manufacturing. Electromagnetic radiation impinging on a fluid medium may interact with the medium by absorption, scattering, or fluorescence. Measurement of transmitted, reflected, scattered, or fluoresced radiation by an appropriate set of detection optics may be used to determine characteristics or properties of the medium such as concentrations of chemical analytes or turbidity.

Several common approaches exist for providing optical access of analyzers and spectrometers to fluid samples. Manual introduction of fluid samples to optical instruments by cuvettes or similar sample containers is a standard method for performing discrete sample measurements. Such containers are often disposable items and the fluid sample introduced to the container is most commonly discarded after measurement, especially if the fluid is drawn from a sterile process. While cuvettes or similar disposable cells may be configured in a motorized tray or carousel assembly to permit automated measurements of several samples, such measurements are of limited value for continuous, long-term monitoring or when high time resolution is required.

Many varieties of fluid cells also exist in the prior art. Unlike cuvette-type approaches, cells permit continuous delivery of fluid to a measurement apparatus. Process cells comprising a machined housing with connectors for optical fibers and inlet/outlet tubing are common prior art examples. These assemblies often comprise parallel window geometries whereby fluid traversing the windows is optically interrogated by electromagnetic energy delivered and collected by optical fibers. Such assemblies are often machined from metal or plastic, are intended to be used multiple times, and are designed to withstand harsh process conditions such as high pressure, high temperature, and extended contact with corrosive solutions. Cells for such demanding environments are typically costly and inconvenient to incorporate in processes that require sterilization of all wetted surfaces. Furthermore, many examples comprise optical materials that are intended for ultraviolet (UV), visible (VIS), and telecommunications wavelengths which span approximately 200 to 1600 nm. Such materials typically have poor optical transmission in infrared wavelengths beyond 1600 nm, and are thus unsuitable for optical instrumentation utilizing that region of the electromagnetic spectrum.

Numerous branches of industry and science increasingly prefer so-called "single-use" or "disposable" components in fluid processing applications. The ease of use of disposable components such as processing vessels and sensors is particularly attractive in, for example, biological applications where sterility is of the upmost importance. Single-use, disposable components may be offered to the end user pre-sterilized, and no costly cleaning procedures are required after the fluid processing has terminated—the user may simply discard the disposable component. It is therefore desirable to design components that come into contact with process fluids as single-use, disposable items if at all possible.

Disposable flow cells have been demonstrated in the art. Some examples are simply less costly plastic analogs to the previously described process cells, but suffer from the same limitations. Other examples utilize a disposable cell assembly situated within optical elements and a housing assembly that may be disassembled such that the flow path is unbroken. Despite the merits of such examples, prior art implementations have often been specific to spectroscopic measurements in the UV and visible electromagnetic spectrum, require inconvenient assembly and disassembly procedures, and are not well-suited for infrared spectroscopic applications.

Another common limitation of prior art cell designs is that assembly and disassembly steps are required in the fluid flow and/or optical paths to connect cells to a process. In the case of common reusable process cells, a typical configuration includes fluid connectors coupled to the cell for attachment of tubing lines to carry the fluid to the measurement zone of the cell. In this configuration, insertion or removal of the cell from the flow path requires coupling or decoupling of the tubing from the connectors. Such manual intervention is often undesirable, especially in closed-loop and sterile processes. Disposable cells, on the other hand, are in some cases able to leave the flow path unbroken during insertion or removal of the cell from the flow path. However, prior art versions require manual assembly and disassembly of mechanical components to access the disposable cell, and this level of user intervention is often undesirable and inconvenient.

To overcome the limitations of prior art methods of optical interfacing with fluid samples, an optical cell apparatus is desired in which the optical path length is stable, all components in the optical path are constructed from materials highly transparent within the spectral range of the analysis, and all materials that contact the fluid are disposable and may be sterilized by common means. The disposable cartridge and tubing contained therein would desirably be of sufficiently low cost to render it a consumable which may be regularly replaced, and replacement should desirably be feasible by unskilled personnel and require minimal, if any, assembly or disassembly of mechanical components. Furthermore, said disposable cartridge may desirably be removable from the optical instrument during a continuous, closed-loop process without compromising any fluid seal or the sterile environment within the cell as well as be capable of being reinserted to resume measurements. The apparatus also would desirably be amenable to both free-space and optical fiber based coupling approaches.

BRIEF SUMMARY

The present invention is directed to an optical apparatus with a single-use, disposable fluid flow cartridge with fluid conduit assembly and optical interface that transmits electromagnetic radiation from an instrument into, in certain implementations, a static or flowing fluid medium, being aqueous or non-aqueous in nature, where it interacts with said medium, and collects the resultant radiation to enable determination of characteristics of the fluid and its constituents by optical analysis with an optical instrument. Various implementations of the invention find application, for example, in biotechnology, clinical chemistry, pharmaceutical research and production, food and beverage manufacturing, and petroleum processing. Certain implementations of the invention may also find application in general optical spectroscopic analyses.

An advantage of certain implementations of the present invention is that one or more optical cells housed within a cartridge can be easily installed or removed from an optical interface without compromising the fluid flow path, even while fluid processing is underway. Furthermore, little or no assembly or disassembly is required to execute installation or removal of said one or more cartridges within said optical interface. This is particularly valuable in fluid processing applications such as bioprocessing and pharmaceutical development and manufacturing where sterility of the fluid must be maintained. Said one or more optical cells of certain implementations of the present invention may be constructed of materials that are compatible with a wide range of optical wavelengths and types of optical measurements. Certain implementations of the present invention, for example, can accommodate measurements at near-infrared wavelengths.

An additional advantage of certain implementations of the present invention over the prior art is that the fluid cells and cartridge may be constructed of disposable materials. Moreover, materials that are tolerant to common sterilization techniques such as autoclave, gamma irradiation, and ethylene oxide, may be chosen for the construction of said cells and cartridge. Utilization of disposable materials that can withstand sterilization is particularly advantageous in biological applications where single-use components and assemblies are gaining favor due to ease of use and reliable sterilization.

These and other features, objects and advantages of the disclosed subject matter will become better understood from a consideration of the following detailed description, drawings, and claims directed to the invention. This brief summary and the following detailed description and drawings are exemplary only, and are intended to provide further explanation of various implementations without limiting the scope of the invention, which is solely as set forth in the claims.

DETAILED DESCRIPTION

As used herein, "cartridge" means a housing, case, cover, enclosure or frame generally used to contain and support one or more sections of tubing or fluidic conduit.

As used herein, "near infrared", "near-infrared", and "NIR" mean the region of the electromagnetic spectrum generally spanning wavenumbers between $3300 \, cm^{-1}$ and $14,000 \, cm^{-1}$ (corresponding to wavelengths of approximately $0.7 \, \mu m$ to $3.0 \, \mu m$), and any wavelengths, bands, and sub-bands falling therein.

As used herein, "interrogation" and "sampling" mean illuminating a sample with optical radiation and collecting at least a portion of the radiation having interacted with said sample for optical analysis.

Figure 1:
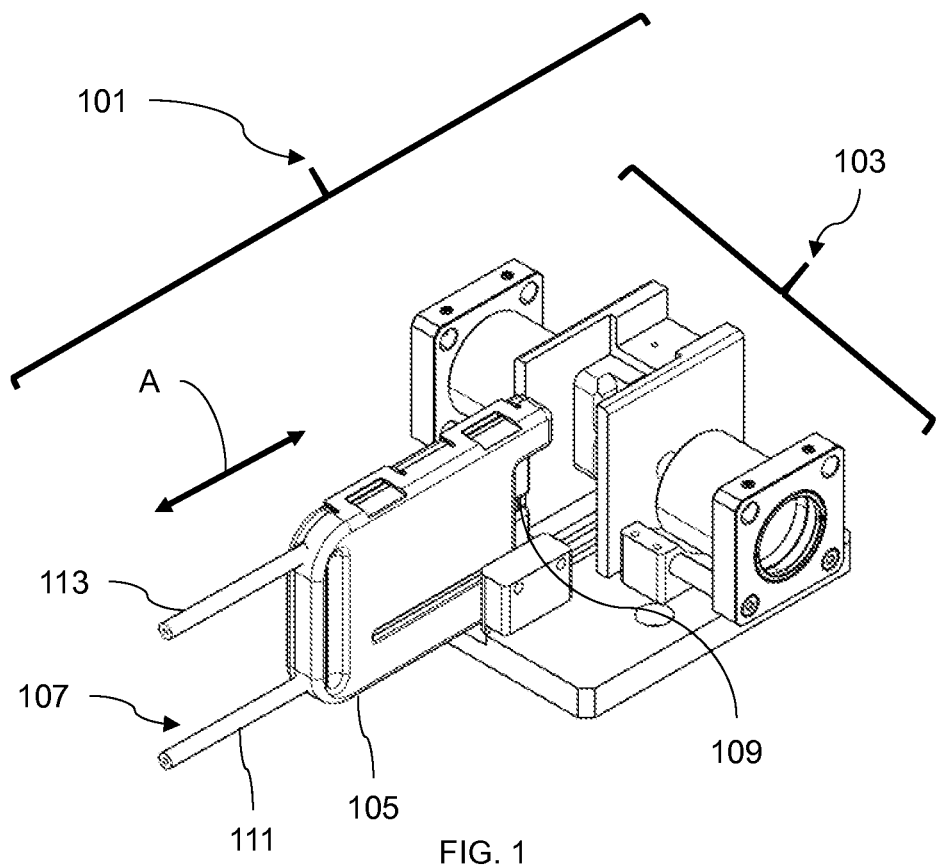
FIG. 1 is an isometric view of one embodiment of the optical apparatus with fluid conduit and disposable fluid cartridge.
Figure 2:
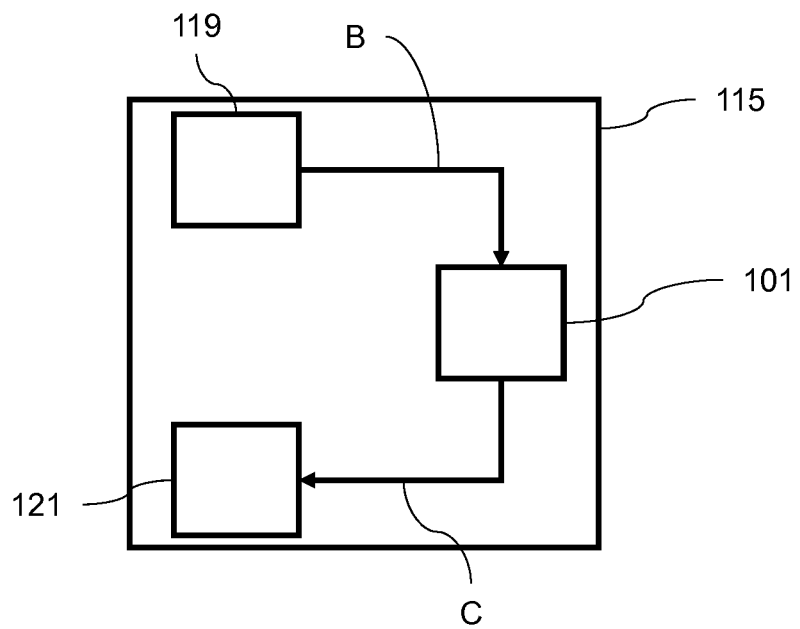
FIG. 2 is a block diagram depicting the arrangement of an optical instrument utilizing the optical apparatus internally.
Figure 3:
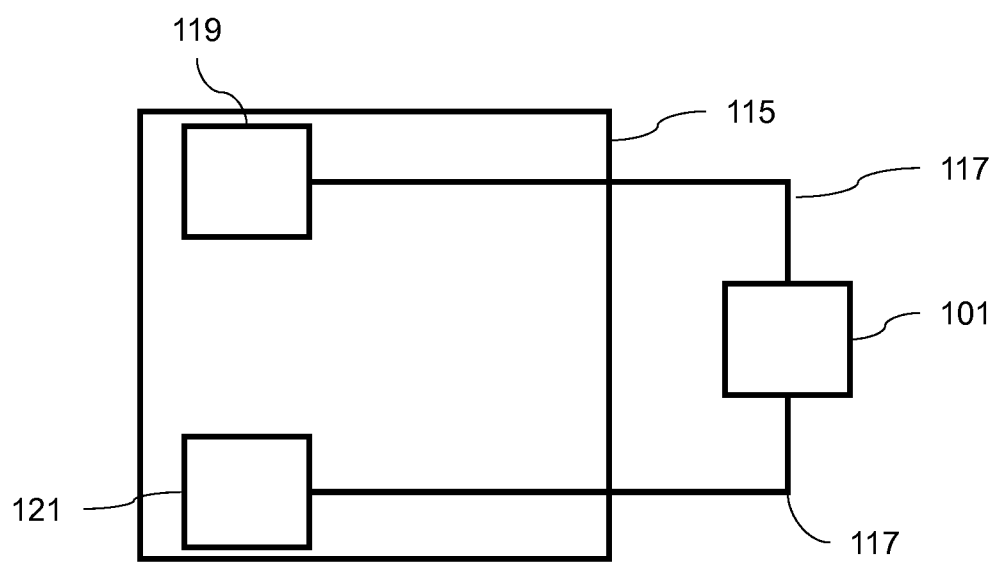
FIG. 3 is a block diagram depicting the arrangement of an optical instrument utilizing the optical apparatus externally and connected via optical fibers.

One embodiment of the optical apparatus 101 is shown in FIGS. 1 to 3. The optical apparatus 101 generally comprises three primary component groups: an optical interface assembly 103, a disposable cartridge serving as a housing 105, and a tubing assembly 107 comprising at least one fluid conduit 109 for optical sampling as well as any requisite fluid delivery 111 and fluid exit tubing 113. The optical apparatus 101 may be directly installed within an optical instrument 115 such as a spectrometer as shown in FIG. 2, or coupled to an instrument using optical fibers 117 as shown in FIG. 3. In FIG. 2, an optical source 119 is used to generate electromagnetic energy, and a portion of said electromagnetic energy generally travels in the direction of arrowed line B. Electromagnetic energy may travel through additional optical elements such as lenses, fibers, mirrors, and a wavelength discriminator (not shown) between the optical source 119 and the optical apparatus 101, as well as between the optical apparatus 101 and the sensor 121 indicated by arrowed line C. The optical apparatus 101 is particularly well-suited to spectroscopic applications, and is able to accommodate a wide range of wavelengths by proper choice of fluid conduit 109 and optical elements within the optical interface assembly 103. The cartridge 105 is generally installed into or removed from the optical interface assembly 103 by translating the cartridge 105 along the direction indicated by double arrowed line A in FIG. 1.

Figure 4:
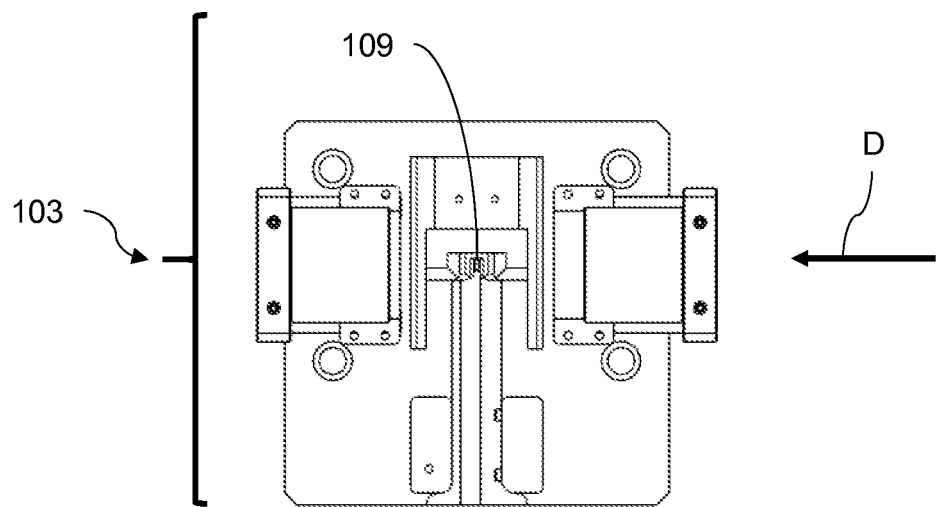
FIG. 4 is a top view of the optical interface assembly.
Figure 5:
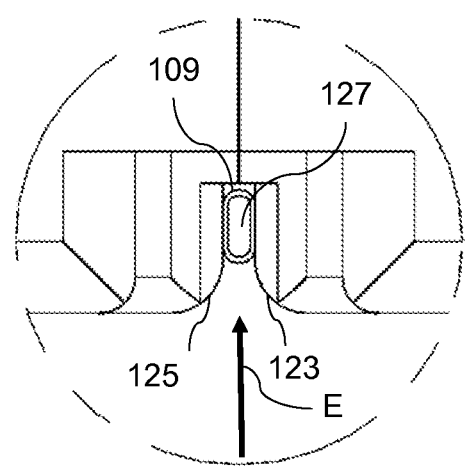
FIG. 5 is a detailed view of the top view of the optical interface assembly near the measurement zone.

A top view of the optical interface assembly 103 is shown in FIG. 4. Electromagnetic energy from an optical instrument 115 (not shown in FIG. 4) may travel for instance in the direction indicated by arrowed line D. The present invention establishes a stable length of optical path through a fluid sample by compressing a fluid conduit 109 at least partially comprised of a material that is at least partially compressible, such as polymer tubing, between at least two surfaces. A detailed view of the optical interface assembly 103 near the region where the fluid conduit 109 is situated when installed with the cartridge 105 (not shown) is shown in FIG. 5. The cartridge 105 containing fluid delivery tubing 111, and fluid exit tubing 113, is not shown in FIG. 4 or FIG. 5 to allow the components of the optical interface assembly 103 to be viewed clearly. The view in FIG. 5 shows the fluid conduit 109 compressed between a first compression surface 123 and a second compression surface 125 that define a measurement zone 127. The fluid conduit 109 may be provided with a generally round cross sectional profile. The distance between an area on the first compression surface 123 and an opposing area on the second compression surface 125 is generally smaller than the original outer diameter of the section of the fluid conduit 109 that is introduced into the measurement zone 127. The action of introducing the fluid conduit 109 with the originally circular cross sectional profile into the optical interface assembly 103 having the compression surfaces 123 and 125 by translating in the direction indicated by arrowed line E acts to deform the fluid conduit 109. After introduction of the fluid conduit 109 into the measurement zone 127, the length of optical path, generally taken as the distance between opposing regions on the first compression surface 123 and second compression surface 125 minus twice the thickness of the wall of the fluid conduit 109, is generally highly stable. In the primary embodiment, the length of optical path is generally on the order of 0.5 mm to 2.0 mm. The length of optical path may be readily modified by appropriate design of the components comprising the first compression surface 123 and second compression surface 125. Additional compression surfaces may also be provided to ensure that the desired shape of fluid conduit 109 and length of optical path within the measurement zone 127 is achieved. It will be obvious to those skilled in the art that a wide range of lengths of optical path, generally between 0.05 mm and 10 mm, may be realized by proper choice of original outer diameter of the fluid conduit 109 and configuration of the optical interface assembly 103 to position the compression surfaces 123 and 125 as needed.

The fluid conduit 109 can be comprised of a wide range of materials, and can be comprised of two or more sections joined together. The section of fluid conduit 109 to be situated within the measurement zone 127 is at least partially compressible and selected according to the range of optical wavelengths to be used in the measurement. In one embodiment, a perfluorinated polymer is chosen due to high transparency in the portion of the near-infrared (NIR) wavelength range spanning 3300 $cm^{-1}$ to 5600 $cm^{-1}$ wavenumbers. Polymers lacking C—H, C—O, N—H and O—H chemical bonds, such as from the Teflon® family of products, are generally good candidate materials in this wavelength range due to the absence of strong optical absorption features. Examples of such polymers include Teflon® polytetrafluoroethylene (PTFE), ethylene tetrafluoroethylene (ETFE), Teflon® fluorinated ethylene propylene (FEP), Teflon® amorphous fluoroplastics (AF), modified fluoroalkoxy (MFA), and Teflon® perfluoroalkoxy copolymer (PFA). For use in wavelength ranges other than the near-infrared, the fluid conduit 109 may be comprised of a plurality of polymer tubing materials. Examples of such materials include polyethylene, polyether ether ketone (PEEK), polyvinyl chloride (PVC), nylon, and polycarbonate.

Figure 6:
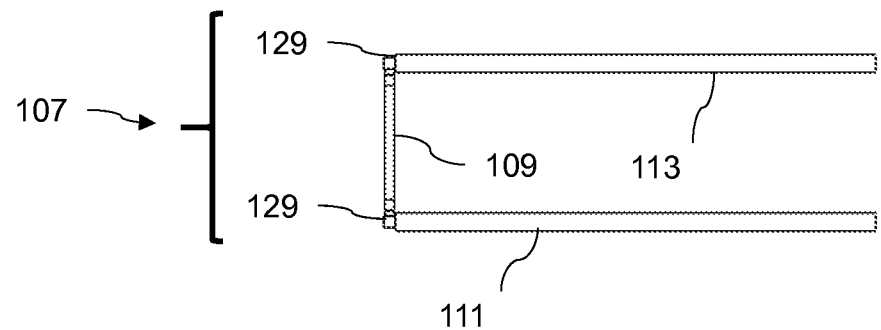
FIG. 6 is a side view of a tubing assembly coupled by connectors.
Figure 7:
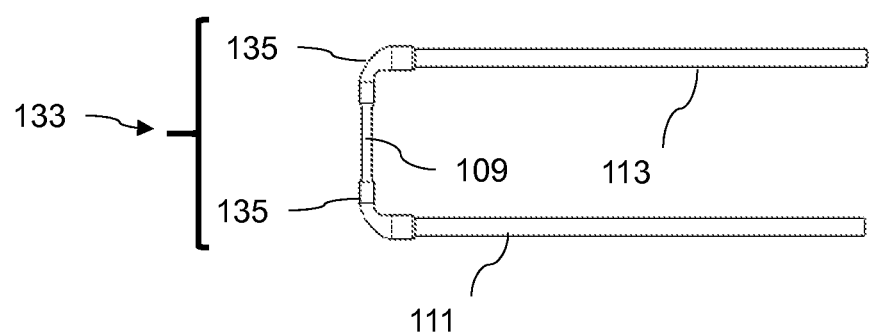
FIG. 7 is a side view of a tubing assembly coupled by overmolded joints.
Figure 8:
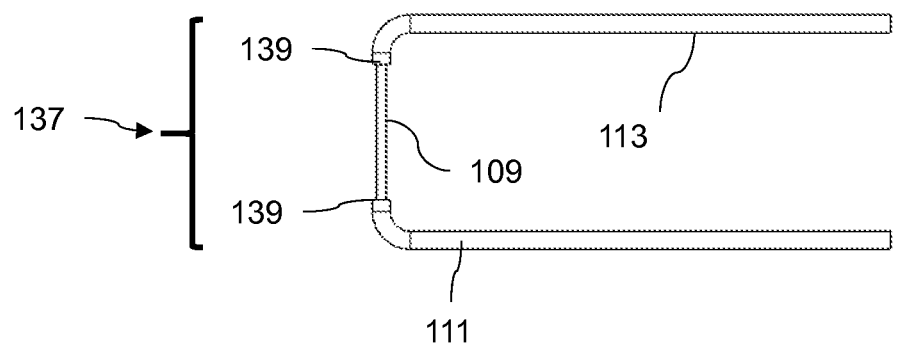
FIG. 8 is a side view of a tubing assembly coupled by welding.

A tubing assembly 107 comprising tubing connectors 129 and a fluid conduit 109 for optical measurement, as well as fluid delivery tubing 111 and fluid exit tubing 113 in fluid communication with said fluid conduit for optical sampling is shown in FIG. 6. Said tubing connectors 129 may comprise, for example, polymers, composites, or metals. Cable ties or other compressive elements (not shown) as well as adhesive bonding may be provided to reinforce the connections between the tubing sections. Two alternative joining methods to connect two or more tubing sections are shown in FIG. 7 and FIG. 8. An example of a tubing assembly joined by overmolding techniques 133 is shown in FIG. 7. In this multi-material molding technique, two or more polymers are used in an injection molding process to provide a robust joint 135 between dissimilar materials. FIG. 8 depicts a welded tubing assembly 137 where the joint 139 between the fluid conduit 109 and fluid delivery 111 and exit 113 tubing components is formed by heat- or adhesive-based welding techniques. Numerous examples of fluid sampling applications, such as biological or pharmaceutical fluid processes, require that all materials that come in contact with the fluid to be evaluated are sterilized. Typical sterilization methods include autoclave or steam (heat) sterilization, gamma irradiation, and ethylene oxide treatment. Materials compatible with these sterilization methods are commonly employed in the present invention to ensure compatibility with biological and pharmaceutical processes.

In another embodiment of the invention, the fluid conduit 109 for optical sampling may further comprise an additional polymer element. Said additional polymer element may be chosen such that it has optical absorption features within the wavelength range of interest that provide a signature whereby the wavelength axis of the measurement may be calibrated. In such a procedure, the wavelength of optical absorption features of said additional polymer can be compared to reference wavelength values of said features from an independent measurement, and adjustments to the wavelength axis of the measurement can be made based upon the comparison. This wavelength reference procedure is highly useful to help minimize optical instrument drift over time, as well as to validate instrument performance.

Figure 9:
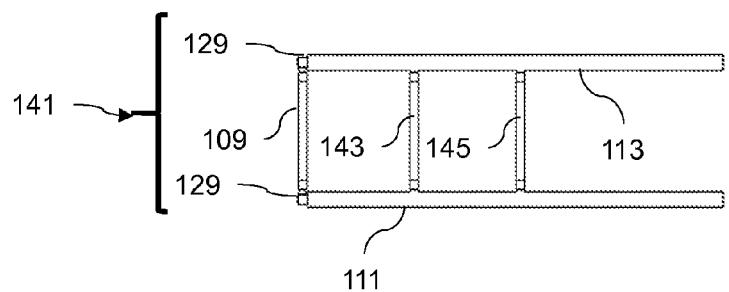
FIG. 9 is a side view of a tubing assembly connected by connectors and comprising multiple fluid conduits for optical sampling.
Figure 10:
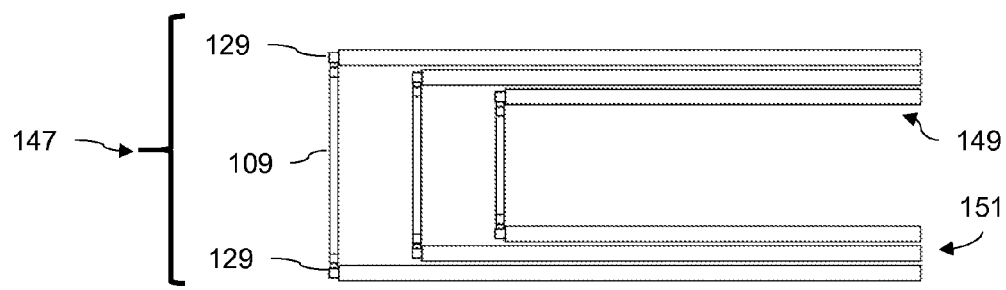
FIG. 10 is a side view of a configuration comprising multiple tubing assemblies in a multiplexed arrangement.

Embodiments of the present invention whereby tubing assemblies are joined with tubing connectors 107, overmolding 133, and welding 137 may be extended to provide multiple fluid conduits 109 for optical sampling. An example of a multiple measurement tubing assembly 141 embodiment where multiple fluid conduits 109 are generally connected to the same fluid delivery tubing 111 and fluid exit tubing 113 with tubing connectors is shown in FIG. 9. In this figure, a second fluid conduit 143 and a third fluid conduit 145 are shown; each may be used for a separate measurement. Such an embodiment provides for performing one or more additional measurements, being optical in nature or otherwise, within one analytical instrument 115. FIG. 10 shows an embodiment where multiple tubing assemblies 107 are provided to enable a multiplexed tubing assembly 147. In this embodiment, the multiplexed tubing assembly 147 may be housed within a single cartridge 105, and measurements on multiple fluid samples may be performed within a single optical instrument 115. A second tubing assembly 149 and a third tubing assembly 151 are shown in FIG. 10 as an exemplary case. Additionally, analysis of a fluid sample may be performed by multiple analytical methods, being optical in nature or otherwise, within a single instrument. For example an analytical instrument may comprise a second analysis module, such as an electrochemical analysis module, to complement an optical measurement. This embodiment finds application, for example, in sampling fluid from multiple fluid sources or from multiple locations within a single fluid source. Analysis of fluid from multiple fluid sources with a single instrument offers the benefit of reducing the per fluid-source cost of analyzing fluid samples. Analysis of fluid samples from multiple locations within a single fluid source provides the ability to monitor the consistency of the property or properties of the fluid being determined within said source. In FIG. 9 and FIG. 10, the fluid conduits for optical sampling 109, 143, and 145 for example need not be comprised of the same material. Construction of the tubing assemblies 141 and 147 using fluid conduits 109, 143, and 145 having different materials provides the ability to perform optical measurement within different wavelength bands. For example, one fluid conduit may be comprised of a material with high transparency in the near-infrared, and another may be comprised of a material with high transparency in the visible spectrum. Embodiments of the cartridge 105 and optical interface 103 may be provided to accommodate multiple measurement tubing assemblies such as 141 and 147 shown in FIG. 9 and FIG. 10, respectively. For example, an optical interface 103 may provide multiple beam paths with corresponding mechanical and optical features. Additionally, a cartridge 105 may be provided with multiple features to provide access to the housed fluid conduits 109. In an embodiment having multiple optical paths, the lengths of the optical paths established by the compression surfaces 123, 125 and fluid conduits 109 need not be identical.

Figure 11:
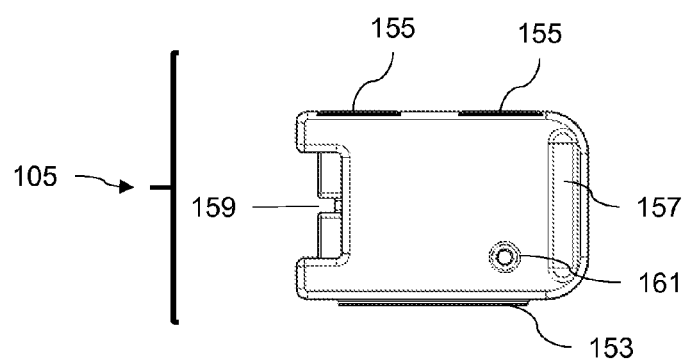
FIG. 11 is a side view of a cartridge housing.
Figure 12:
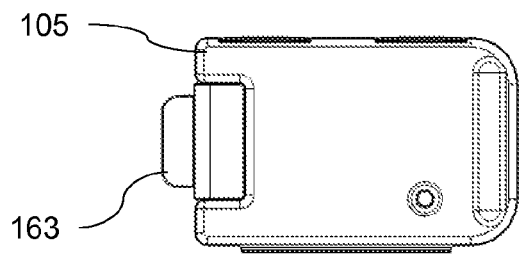
FIG. 12 is a side view of a cartridge housing with a protective clip.
Figure 13:
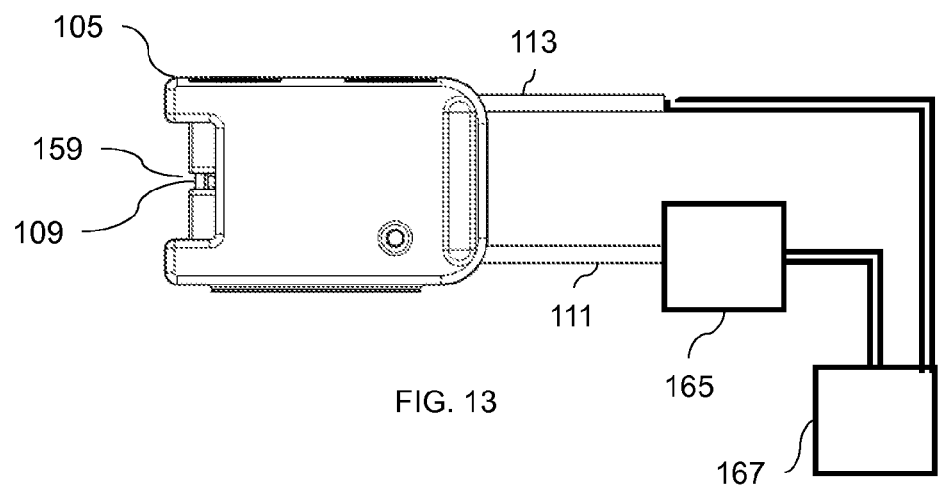
FIG. 13 is a side view of a cartridge housing, fluid-containing vessel, and transfer pump.
Figure 14:
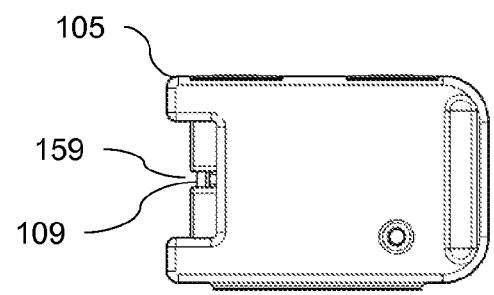
FIG. 14 is a side view of a cartridge housing with a sealed fluid conduit.

The cartridge serving as a housing 105 for the fluid conduit 109 and optionally partially enclosing the fluid delivery tubing 111 and fluid exit tubing 113 is shown in FIGS. 11 to 14. A side view of an empty cartridge 105 is shown in FIG. 11. The cartridge 105 provided in the present invention is generally comprised of a polymer such as polyethylene or polypropylene, though may also be comprised of other polymers, metals, composites, or a combination thereof. In one embodiment, the cartridge 105 is comprised of a polymer and is preferably manufactured by injection molding. Injection molding accommodates highly consistent part manufacturing, and allows the cartridge 105 to be fabricated as a single piece coupled by a living hinge 153 and snap-fit fasteners 155. A recess 159 in the cartridge 105 is provided for access of the compression surfaces 123 and 125 to the fluid conduit 109 housed within the cartridge 105. In one embodiment, a single recess 159 is provided for access to the fluid conduit 109, though other embodiments may provide multiple recesses 159 such that fluid within the fluid conduit may be sampled in multiple measurement zones 127. A depressed area forming a grip 157 is provided for manipulating the cartridge 105 into the optical interface assembly 103. Retention of the cartridge 105 within the optical interface assembly 103 may be implemented with a locking mechanism, such as a recess 161 to accommodate a pin (not shown). FIG. 12 shows a side view of the cartridge 105 with an optional protection clip 163. The protection clip 163 serves to protect the fluid conduit 109 prior to installation into the optical interface assembly 103, for example during sterilization processes and handling. FIG. 13 shows a side view of the cartridge 105 with the tubing assembly 107 installed. The fluid conduit 109 for optical sampling is visible within the recess for tubing access 159, and portions of the fluid delivery tubing 111 and fluid exit tubing 113 are also shown. The present invention offers multiple configurations for delivery of fluid to the fluid conduit 109. In FIG. 13, a fluid pump 165 is shown connected to the fluid delivery tubing 111 and a fluid source 167. The fluid pump 165 may be a manual pump such as a syringe, or a powered pump mechanism such as a motorized syringe pump, a peristaltic pump, a vacuum pump, a gas pressure actuator, or an autosampler. An autosampler is a device configured to automatically draw a fluid sample from a container and deliver the fluid sample to an analytical instrument. Autosamplers may be configured to sample fluid from one or more containers, and deliver fluid samples to one or more analytical instruments. Fluid may be automatically drawn by the fluid pump 165 from a fluid source 167 and delivered to the fluid conduit 109 by the fluid delivery tubing 111. The fluid source 167 may comprise a wide range of vessels, containers, and conduits. Examples of the fluid source 167 include a bioreactor, a chemical reactor, a flexible polymer container, a pipe, and a flask. After passing through the fluid conduit 109, the fluid may be returned to the fluid source 167 by way of the fluid exit tubing 113, or be transferred to an alternate destination. Fluid may be continuously circulated through the fluid conduit 109, or intermittently delivered to the fluid conduit 109 depending on the nature of the process being monitored. In another embodiment, the fluid conduit 109 may be substantially sealed and have no fluid delivery tubing 111 or fluid exit tubing 113 attached as shown in FIG. 14. In this manner, discrete samples may be introduced into an optical instrument 115.

Given the strict sterilization requirements for materials that come into contact with process fluids in many applications, particularly in the biotechnology and pharmaceutical industries, there is an accelerating trend towards use of components that are intended for only a single use. Examples of such single-use components include pH sensors, dissolved oxygen (DO) sensors, fluid sampling tubing, and even the processing vessels themselves. Such single-use components are commonly intended to be sterilized (often by the manufacturer), used for a single process, and subsequently discarded. Components intended to be used only one or few times are often interchangeably called "single-use," "disposable," and "consumable." Quite often it is the case that such single-use components offer cost savings over multiple-use analogs due to reduced set-up time before a process and cleaning time and cost after a process. In certain implementations of the present invention, the assembly comprising the tubing assembly 107 and cartridge 105 is configured as a single-use assembly. As stated previously, the cartridge 105 may be manufactured out of common polymers by injection molding. The injection molding process is capable of yielding high quantities of identical parts at low cost. Furthermore, the cartridge 105 may be comprised of polymers that are tolerant to common sterilization procedures. The tubing assembly 107 comprising the fluid conduit 109 and optionally the fluid delivery tubing 111 and fluid exit tubing 113 may also be manufactured from materials that are both of sufficiently low-cost and tolerant to common sterilization procedures. As the cartridge 105 and tubing assembly 107 may be manufactured from inexpensive materials and by inexpensive methods, they may commonly be considered single-use or disposable items. As used herein, the terms "single-use," "inexpensive," and "disposable" will be understood to mean that one or more of the following conditions are substantially true: the cost of the described items is generally lower than the cost, including labor, of cleaning, sterilizing, and re-certifying said items; the cost the described items is generally lower than 15% of the overall cost, including labor, of the entire process; and the cost of the described items is generally less than or equal to the cost of performing an analogous measurement, such as manual single-point discrete sampling and analysis, throughout the course of the process. The cost of performing an analogous measurement may be for example the entire cost, including labor, of manually collecting, preparing, and measuring individual samples with a method yielding generally similar information as that provided by the optical instrument 115 utilizing the optical apparatus 101.

Figure 15:
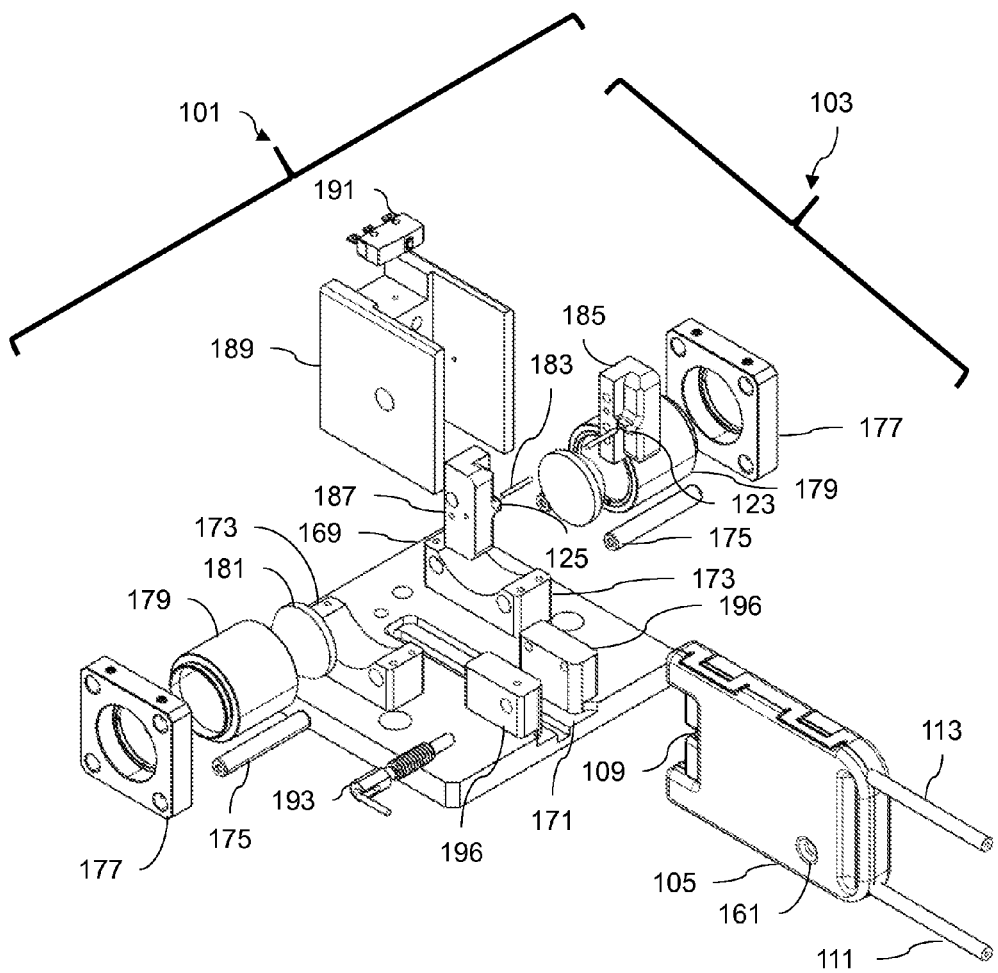
FIG. 15 is an exploded isometric view of an optical apparatus.

An exploded isometric view of one embodiment of the optical apparatus 101 is shown in FIG. 15. The mechanical foundation of the optical interface assembly 103 is a base plate 169 that functions as a fixture for hardware and optical components as well as provides a guide channel 171 for installation of the cartridge housing 105. Support features 173 are provided for optical cage rods 175 (for example Thorlabs model ER1.5) to which optical cage plates 177 (for example Thorlabs model CP02) are attached. Lens tubes 179 (for example Thorlabs model SM1L10) housing lenses 181 are installed into the optical cage plates 177. A central support member 189 provides a mounting platform for a first compression block 185 and a second compression block 187 that house optical waveguides 183. Said compression blocks 185 and 187 comprise said first compression surface 123 and second compression surface 125 used to compress said fluid conduit 109. Said central support member 189 also provides light shielding to prevent stray light from being collected. A position sensor 191 may be attached to the central support member 189 to determine if the cartridge housing 105 has been properly seated within the optical interface assembly 103. The cartridge housing 105 may be secured within the optical interface assembly 103 by use of a locking pin 193 that engages with the recess for locking pin 161 on said cartridge housing 105 and locking pin blocks 196.

In the above described embodiment of the optical interface assembly 103, it will be understood that various optical elements such as parabolic mirrors may be substituted for the lenses 181, and that the optical path through the optical interface assembly 103 need not be straight and may include various steering optical elements. Correspondingly, the described hardware such as the optical interface baseplate 169 may be configured to accommodate such modifications. The optical elements such as lenses 181 and optical waveguides 183 may be chosen to best suit the wavelength range of interest and desired length of optical path through the fluid sample.

Figure 16:
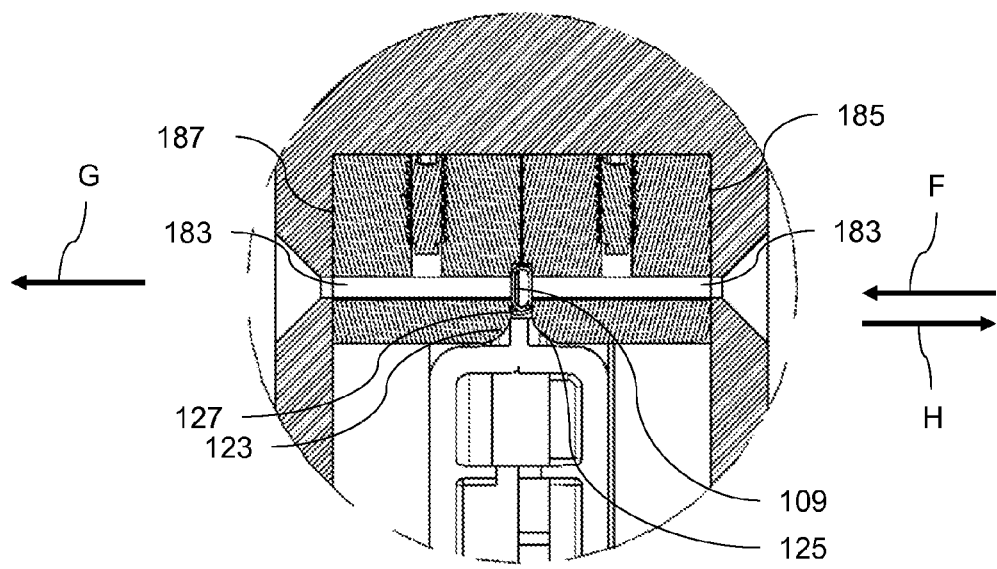
FIG. 16 is a detailed cross sectional view showing the measurement zone.

FIG. 16 shows a detailed cross sectional view of the optical interface assembly 103 housing the optical waveguides 183. The optical waveguides 183 serve to couple electromagnetic energy into and out of the fluid conduit 109 contained within the measurement zone 127. Surfaces of said optical waveguides 183 near the measurement zone 127 may be generally coplanar with the first compression surface 123 and second compression surface 125. Surfaces of said optical waveguides 183 may also protrude beyond said first compression surface 123 and second compression surface 125 such that the optical waveguides 183 themselves define an optical path by means of compression. Said optical waveguides 183 may comprise for example optical rods, optical fibers, or hollow waveguides, and may be chosen such that optical transparency is satisfactory over the wavelength range of interest. Said optical waveguides 183 may optionally comprise optical surface treatments such as anti-reflective coatings to maximize optical transmission, or metallic coatings to reflect at least part of an optical beam. Optical waveguides 183 may comprise hollow waveguides, for example metal or glass tubes preferably having a highly reflective coating in the tubing bore such as nickel tubes with gold plating on the interior surface. The present invention provides for both optical transmission and optical transflection measurements. In FIG. 16, at least a portion of electromagnetic energy incident generally in the direction of arrowed line F enters the fluid conduit 109 within the measurement zone 127 by means of one optical waveguide 183, and at least a portion of the electromagnetic energy having interacted with the fluid sample within the fluid conduit 109 is communicated from the measurement zone 127 by an optical waveguide 183 as depicted by arrowed line G. In this embodiment, electromagnetic energy generally having traversed the measurement zone 127 one time is communicated to the optical instrument 115 to provide an optical transmission measurement. In another embodiment, at least a portion of electromagnetic energy incident generally in the direction of arrowed line F enters the fluid conduit 109 within the measurement zone 127 by means of one optical waveguide 183, and at least a portion of electromagnetic energy having interacted with the fluid sample within the fluid conduit 109 is reflected and communicated from the measurement zone 127 by means of the same optical waveguide 183 generally in the direction indicated by arrowed line H. In this embodiment, the reflected portion of the electromagnetic energy may comprise electromagnetic energy reflected from the fluid sample and suspended material within the fluid conduit 109 as well as electromagnetic energy reflected from the second compression surface 125 that may have an optical waveguide 183 or other optical element embedded within. This embodiment provides an optical transflection measurement whereby a portion of collected electromagnetic energy results from reflection from the fluid sample and materials therein, and a portion of the collected electromagnetic energy results from transmission through the sample.

Figure 17:
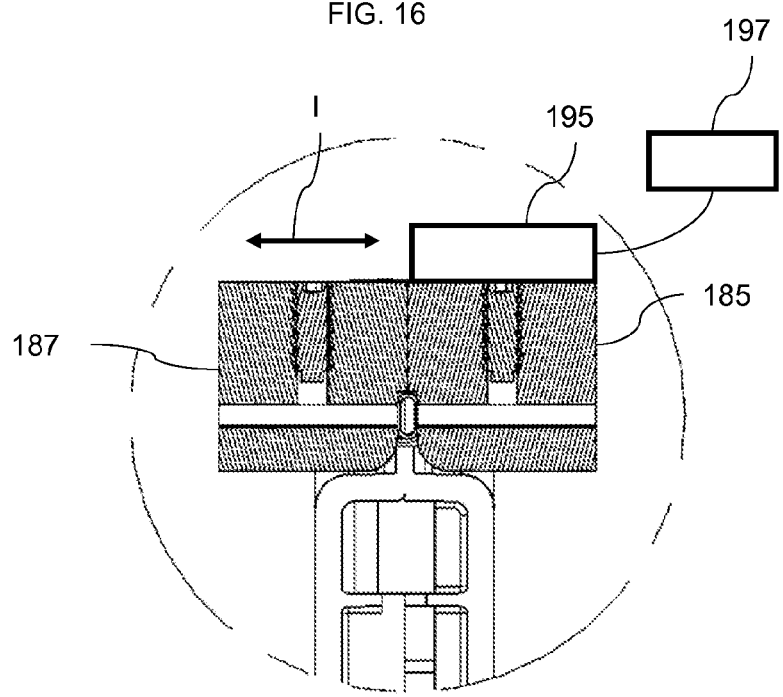
FIG. 17 is a detailed cross sectional view showing the measurement zone, an actuator, and a controller.

In one embodiment of the invention, the length of optical path within the measurement zone 127 is adjustable. The length of optical path may be controlled manually, for example by a screw or other translation means, or automatically by an actuator and a controller. FIG. 17 shows an embodiment where the length of optical path is adjustable. An actuator 195 attached to one or more compression blocks 185, 187 may be controlled by a controller 197 that is operatively connected to the actuator 195 to translate said one or more compression blocks 185, 187 in a direction indicated by double arrowed line I to manipulate the length of optical path in the measurement zone 127. Modification of the length of optical path may be used to accommodate measurement of fluids with different properties such as absorption or turbidity. For example, if a fluid becomes highly turbid during processing, the length of optical path may be decreased in order to increase the amount of electromagnetic energy available to the optical instrument 115. Conversely, if the level of a substance to be measured in a fluid is low, and an increased interaction length with the fluid sample is desired to increase absorption by the substance, the length of optical path may be increased. Automatic variation of the distance between the first compression surface 123 and second compression surface 125 and thereby the length of optical path may also be used to assist in clearance of entrapped material or gas bubbles within the measurement zone.

Figure 18:
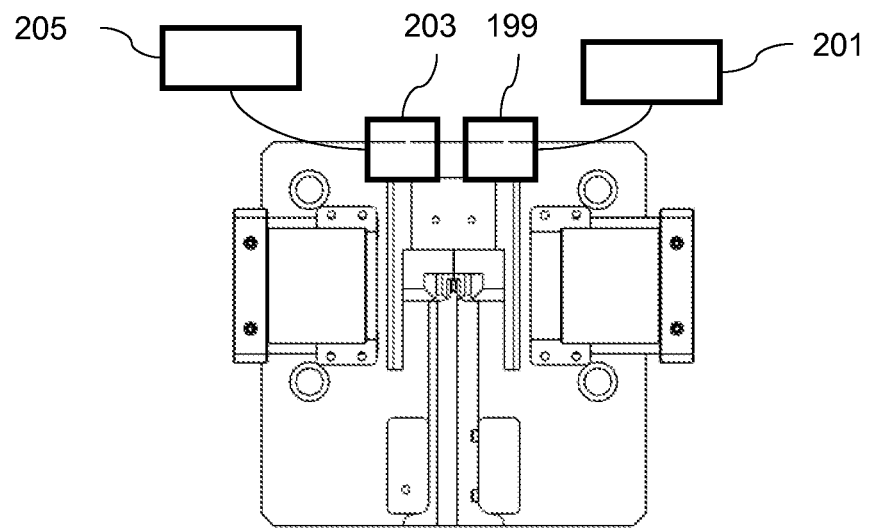
FIG. 18 is a top view of an embodiment of the optical interface assembly including a temperature control element, an electromechanical agitator, and controllers for both.

The optical interface assembly 103 may also comprise auxiliary components to provide additional functionality to the optical apparatus 101. FIG. 18 shows an embodiment of the optical interface assembly 103 further comprising an optional temperature control assembly 199. Said temperature control assembly may comprise at least one of a heater or a cooler, and may further comprise a controller 201 for said at least one of a heater or cooler. The optical interface assembly may further comprise an electromechanical agitator assembly 203 and corresponding controller 205. Said electromechanical agitator 203 may comprise for example a vibrating motor or piezoelectric transducer in contact with at least a portion of the optical interface assembly 103. Provision of an electromechanical agitator 203 enables manual or automatic agitation of the optical interface assembly 103 and fluid conduit 109 housed therein for the purposes of for instance dislodging gas bubbles that have become entrapped within the measurement zone 127. Provision of at least one of a heater or cooler enables control of the temperature of the fluid sample within the fluid conduit 109 when positioned in the measurement zone 127.

Figure 19:
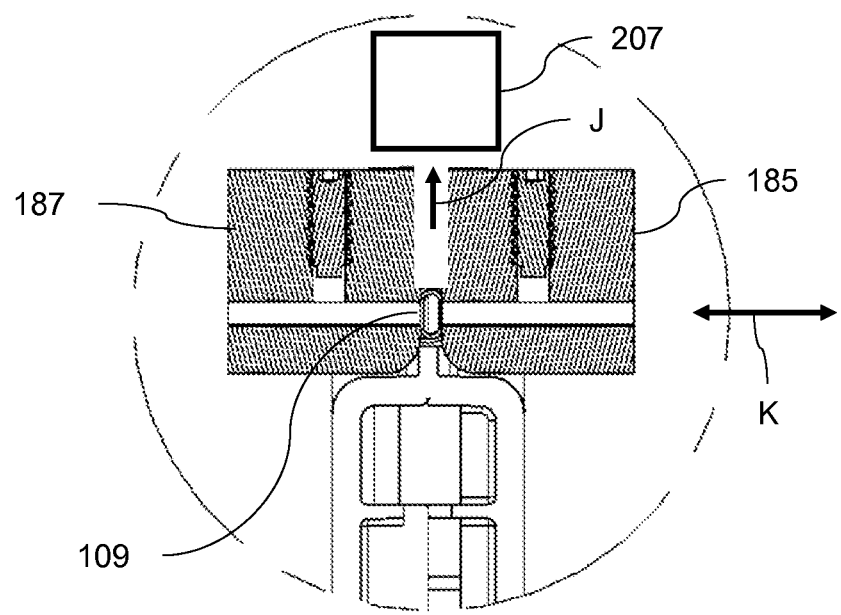
FIG. 19 is a detailed cross sectional view showing an embodiment of the measurement zone including a second optical path that is off-axis from the primary optical path.

In yet another embodiment, the optical interface assembly 103 may further comprise a second optical path whereby electromagnetic energy may be collected in a direction that is substantially off-axis from the first optical path. FIG. 19 shows such an embodiment where the second optical path indicated by arrowed line J is substantially off-axis from a first optical path indicated by double arrowed line K. At least a portion of the electromagnetic energy in the off-axis path indicated by arrowed line J is collected by one or more optical elements 207. Collection of electromagnetic energy in an off-axis geometry provides for example for scattering measurements to be performed. An example of such a scattering measurement is a turbidity measurement, whereby material suspended within a fluid sample in the fluid conduit 109 scatters a portion of the incident electromagnetic energy in one or more directions substantially off-axis from the primary optical axis.

A method of performing an optical measurement on a fluid sample with the optical apparatus 101 is provided. A cartridge 105 that houses at least a fluid conduit 109 and optionally partially houses fluid delivery tubing 111 and fluid exit tubing 113 is situated within the optical interface assembly 103 such that the cartridge 105 substantially positions the fluid conduit 109 within the measurement zone 127 comprising the first compression surface 123 and second compression surface 125. The fluid conduit 109, being at least partially compressible, is compressed by said first compression surface 123 and second compression surface 125 to provide a defined length of optical path through a fluid sample contained therein. The optical interface assembly 103 may be positioned internally within an optical instrument 115 or external to said optical instrument 115 and connected by one or more optical fibers 117. At least a portion of the electromagnetic energy provided by the optical instrument 115 is collected after interaction with the fluid sample contained within the fluid conduit 109 and subsequently provided to the optical instrument 115 for analysis. The fluid sampled by the optical apparatus 101 and analyzed by the optical instrument 115 may originate from a plurality of processes including but not limited to fluid processing, fluid handling, fluid storage, instrument calibration, and instrument calibration assessment.

Figure 20:
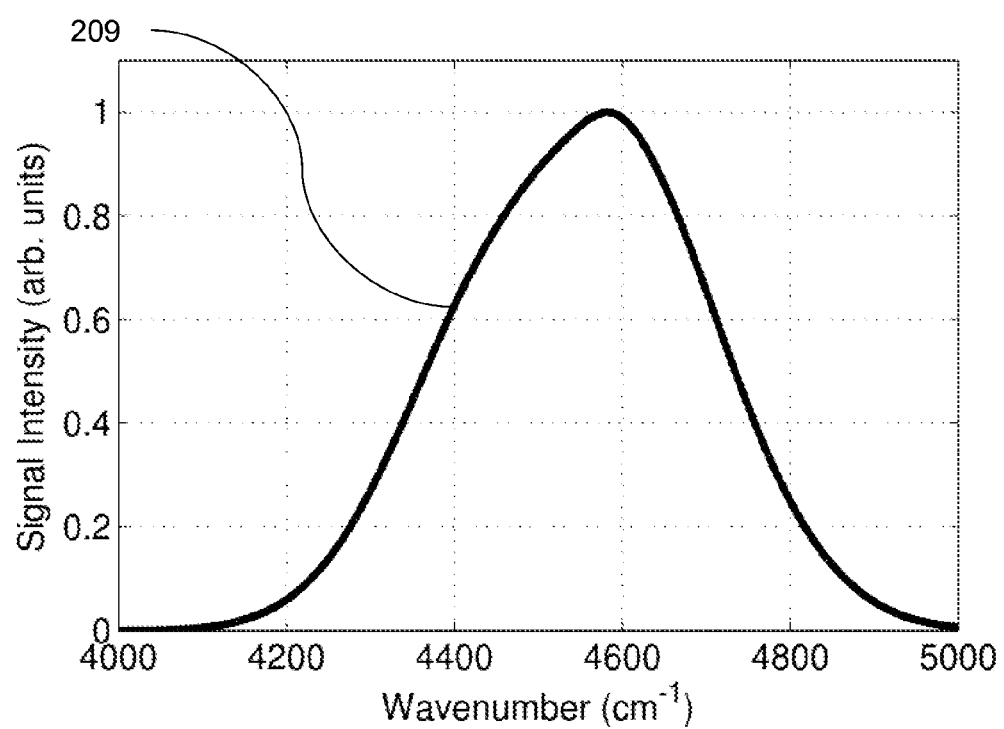
FIG. 20 shows an example of a transmission spectrum of water acquired with the invention in the near-infrared spectral range.

Results of an experiment employing an embodiment of the present invention are presented in FIG. 20. The experimental graph in FIG. 20 shows a near-infrared transmission spectrum 209 of water taken with the present invention situated within an optical instrument. A tungsten halogen light source was used in the optical instrument, and the length of optical path within the fluid conduit 109 was approximately 1.0 mm. In FIG. 20, the x-axis is given in wavenumbers with a range of approximately 4000-5000 $cm^{-1}$, corresponding to 2.0-2.5 µm, and the y-axis is given in arbitrary units. The transmission measurement demonstrates the utility of the near-infrared spectral range for performing measurements in aqueous solutions—even at a path length of approximately 1.0 mm, high quality transmission spectra are obtained with the present invention.

Figure 21:
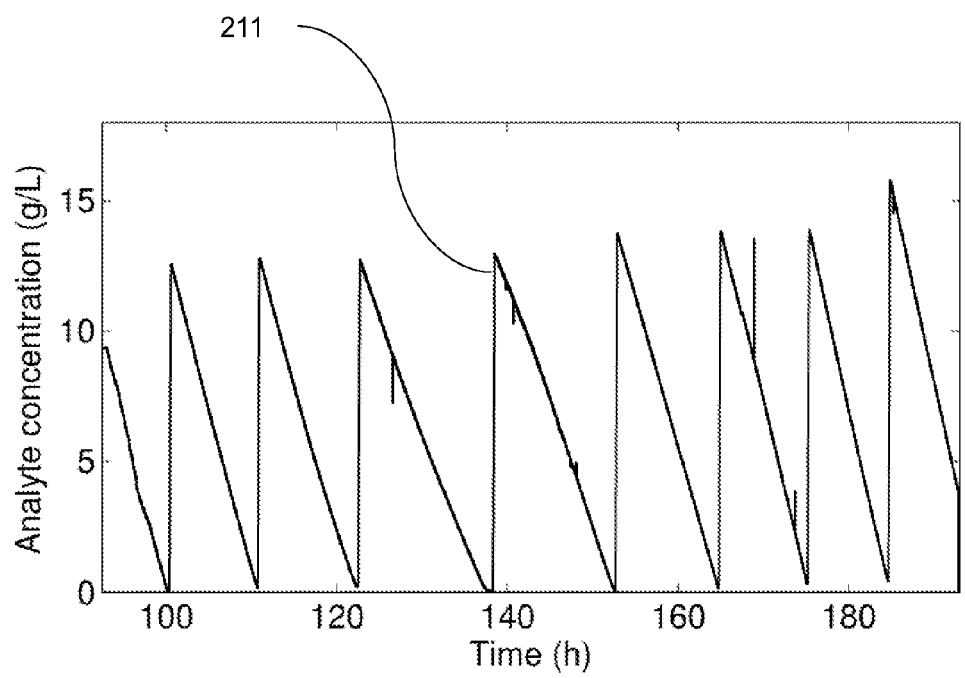
FIG. 21 shows a data plot of the concentration of methanol measured continuously with an embodiment of the present invention used during a *Pichia pastoris* bioreactor fermentation.

An experiment employing an embodiment of the present invention in an optical instrument configured to continuously measure chemical analytes during bioprocessing fermentations by circulating fluid from the process through an embodiment of the present invention is shown in FIG. 21. The solid line 211 is the concentration profile of methanol measured during a *Pichia pastoris* bioprocess—a window of that process spanning approximately 100 hours is shown, however the process lasted in excess of 190 hours, or eight days. This experiment demonstrates the utility of the present invention in optically interrogating fluid processes continuously and for extended periods of time.

Particular examples of fluids that may be analyzed by the method described above include fluids from bioprocesses, chemical processes, fuel production and analysis processes, enzyme production and analysis processes, and food and beverage manufacturing processes. Fluids introduced into the fluid conduit 109 need not be filtered in many cases, allowing analysis of fluid components such as chemical analytes, as well as suspended materials such as cells or particles, simultaneously. Fluid samples may be for example static or flowing, allowing analysis of single samples as well as monitoring of continuous processes. In applications such as bioprocessing, fluid samples may be drawn from upstream processes such as bioreactor fermentations and cell cultures, or from downstream processes such as filtration, purification, and formulation. The optical apparatus 101 is compatible with numerous optical wavelength ranges, and can generally be configured to support a desired wavelength range by appropriate choice of fluid conduit 109, optical waveguides 183, and lenses 181. Alternative optical elements such as mirrors may be substituted for the lenses 181 depending on the parameters of the configuration. In one embodiment of the invention, the optical apparatus is configured to operate in the near infrared spectral range spanning approximately 3300 $cm^{-1}$ to 5600 $cm^{-1}$ (corresponding to wavelengths of approximately 1.8 µm to 3.0 µm).

The present invention has been described with reference to the foregoing specific implementations. These implementations are intended to be exemplary only, and not limiting to the full scope of the present invention. Many variations and modifications are possible in view of the above teachings. The invention is limited only as set forth in the appended claims. All references cited herein are hereby incorporated by reference to the extent not inconsistent with the disclosure herein. Unless explicitly stated otherwise, flows depicted herein do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims. Any disclosure of a range is intended to include a disclosure of all ranges within that range and all individual values within that range.

The invention claimed is:

1. An optical apparatus for examination of a fluid sample, said optical apparatus comprising:
   a. a first compression surface and a corresponding second compression surface defining a measurement zone therebetween;
   b. a fluid conduit situated within said measurement zone, said fluid conduit having at least a portion comprising a material being at least partially transparent at one or more wavelengths, said fluid conduit further comprising at least one section that is at least partially compressible;
   c. a housing containing said fluid conduit whereby said fluid conduit is within said measurement zone; and
   d. one or more optical elements for communicating electromagnetic radiation between said measurement zone and an instrument;
   whereby a length of an optical path of the electromagnetic radiation passing through the fluid conduit is defined by compression of the partially compressible section of the fluid conduit between the first compression surface and the second compression surface.

2. The optical apparatus of claim 1, further comprising a fluid delivery tubing and a fluid exit tubing in fluid communication with said fluid conduit.

3. The optical apparatus of claim 2, wherein said fluid inlet and fluid outlet comprise materials able to withstand sterilization by autoclave, gamma irradiation, or ethylene oxide.

4. The optical apparatus of claim 2 further comprising a pump system connected to one or more of said fluid conduits to communicate fluid from a fluid source to said fluid conduit.

5. The optical apparatus of claim 4, wherein said pump system is selected from the group consisting of a syringe, syringe pump, peristaltic pump, vacuum pump, gas pressure actuator, and autosampler.

6. The optical apparatus of claim 1, wherein said electromagnetic radiation comprises near infrared radiation.

7. The optical apparatus of claim 6, wherein said near infrared radiation comprises wavenumbers between 3300 $cm^{-1}$ and 5600 $cm^{-1}$.

8. The optical apparatus of claim 1, wherein said fluid conduit comprises a polymer lacking C—H bonds, lacking C—O bonds, lacking O—H bonds, and lacking N—H bonds.

9. The optical apparatus of claim 8, wherein said fluid conduit is at least partially comprised of perfluorinated polymer tubing selected from the group consisting of polytetrafluoroethylene (PTFE), ethylene tetrafluoroethylene (ETFE), fluorinated ethylene propylene (FEP), amorphous fluoroplastics (AF), and perfluoroalkoxy copolymer (PFA).

10. The optical apparatus of claim 1, wherein said fluid conduit is comprised of two or more tubing sections joined by one or more of welding, overmolding, adhesive bonding, metallic connectors, or polymer connectors.

11. The optical apparatus of claim 1, wherein said fluid conduit is comprised of a material able to withstand sterilization by one or more of autoclave, gamma irradiation, or ethylene oxide.

12. The optical apparatus of claim 1, wherein said fluid conduit comprises at least a second material having an absorption spectrum being variable between at least two wavelengths whereby a wavelength reference is provided.

13. The optical apparatus of claim 1, wherein said housing comprises one or more of a polymer, a metal, or a composite.

14. The optical apparatus of claim 1, wherein said measurement zone is defined by two optical waveguides.

15. The optical apparatus of claim 1, wherein the optical path traverses at least one of said fluid conduits such that at least a portion of said electromagnetic radiation traverses said measurement zone by communication from one of said compression surfaces to the other of said compression surfaces to provide an optical transmission measurement.

16. The optical apparatus of claim 1, wherein the optical path traverses at least one of said fluid conduits and at least a portion of said electromagnetic radiation traverses at least one of said measurement zones by communication from one of said compression surfaces to the other of said compression surfaces, and at least a portion of the resultant electromagnetic radiation is reflected from said second compression surface back to said first compression surface to provide an optical transflection measurement.

17. The optical apparatus of claim 1, wherein said optical path length is in the range of 0.05 mm to 10 mm.

18. The optical apparatus of claim 17, wherein said optical path length is in the range of 0.5 mm to 2.0 mm.

19. The optical apparatus of claim 1, wherein said fluid conduit is substantially sealed to retain the fluid sample.

20. The optical apparatus of claim 1, wherein said optical apparatus further comprises an electromechanical agitator configured to clear entrapped gas bubbles from said measurement zone.

21. The optical apparatus of claim 20, whereby said electromechanical agitator comprises a vibrating motor or a piezoelectric transducer.

22. The optical apparatus of claim 1, whereby a temperature of the fluid sample is controlled by at least one of a heater or a cooler.

23. The optical apparatus of claim 1, wherein said measurement zone establishing said optical path length comprises an actuator for varying said optical path length.

24. The optical apparatus of claim 23, further comprising a controller in communication with said actuator.

25. The optical apparatus of claim 1 further comprising a second fluid conduit fluidically connected to the fluid conduit and an analysis module adjacent to the second fluid conduit.

26. The optical apparatus of claim 1, wherein the one or more optical elements are positioned to communicate electromagnetic radiation between said measurement zone and the instrument along at least a first optical path and a second optical path, wherein the second optical path is off-axis with respect to the first optical path.

27. A method of performing an optical measurement on a fluid sample, said method comprising the steps of:
   a. compressing a portion of a fluid conduit between at least two compression surfaces to form a defined optical path length between two optical elements;
   b. introducing the fluid sample into said fluid conduit;
   c. coupling electromagnetic radiation into said fluid sample by directing said electromagnetic radiation into one of the optical elements;
   d. collecting at least a portion of said electromagnetic radiation having interacted with said fluid sample; and
   e. analyzing said portion of said electromagnetic radiation with an optical instrument.

28. The method of claim 27, wherein said fluid sample is drawn from a container being used for processing, handling, storage, instrument calibration, or instrument calibration assessment.

29. The method of claim 27, wherein said fluid is drawn from a pharmaceutical process, a fuel process, a food process, a beverage process, an enzyme process, or a chemical process.

30. The method of claim 27, wherein said fluid sample is static.

31. The method of claim 27, wherein said fluid sample is flowing.

32. The method of claim 27, wherein said fluid is drawn from a bioreactor.

33. The method of claim 27, wherein said electromagnetic radiation is in the near-infrared region.

34. The method of claim 27, wherein said electromagnetic radiation comprises wavenumbers between 3300 $cm^{-1}$ and 5600 $cm^{-1}$.

* * * * *